United States Patent [19]

Beremand et al.

[11] Patent Number: 4,880,747

[45] Date of Patent: Nov. 14, 1989

[54] FUSARIUM SPOROTRICHIOIDES MUTANT STRAIN CAPABLE OF PRODUCING BOTH DIDEACETYLCALONECTRIN AND DEACETYLCALONECTRIN

[75] Inventors: Marian N. Beremand; Patricia J. Black, both of Peoria, Ill.

[73] Assignee: The United States of America as represented by the Secretary of Agriculture, Washington, D.C.

[21] Appl. No.: 173,910

[22] Filed: Mar. 28, 1988

[51] Int. Cl.$^4$ .................. C12N 1/14; C12N 1/77; C12P 5/00; C12P 1/02

[52] U.S. Cl. ................................ 435/254; 435/166; 435/171; 435/929

[58] Field of Search ................ 435/166, 171, 254, 929

[56] References Cited

PUBLICATIONS

A. E. Desjardins et al., "Ancymidol Blocks Trichothecene Biosynthesis and Leads to Accumulation of Trichodiene in *Fusarium sporotrichioides* and *Gibberella pulicaris*," Appl. Enviorn. Microbiol., 53: 1860–1865 (1987).

M. N. Beremand, "Isolation and Characterization of Mutants Blocked in T-2 Toxin Biosynthesis," Appl. Environ. Microbiol., 53: 1855–1859 (1987).

R. Greenhalgh et al., "Production and Characterization of Deoxynivalenol and Other Secondary Metabolites of *Fusarium culmorum* (CMI 14764, HLX 1503)," J. Agric. Food Chem., 34: 98–102 (1986).

R. Greenhalgh et al., "Minor Metabolites of *Fusarium roseum* (ATCC 28114)," J. Agric. Food Chem., 32: 1261–1264 (1984).

C. J. Carter and M. Cannon, "Structural Requirements for the Inhibitory Action of 12,13–Epoxytrichothecenes on Protein Synthesis in Eukaryotes," Biochem. J., 166: 399–409 (1977).

S. Nozoe et al., "The Structures of Trichodiol and Trichodiene," Tetrahedron, 28: 5105–5111 (1972).

D. Gardner et al., "Calonectrin and 15–Deacetylcalonectrin, New Trichothecanes from *Calonectria nivalis*," J. C. S. Perkin I, pp. 2576–2578 (1972).

W. P. O. Marasaas et al., In "Toxigenic Fusarium Species, Identity and Mycotoxicology," pp. 7, 154–155, The Pennsylvania State University Press (1984).

Biotech 86-05721, Greenhalgh et al, J. Agric. Food Chem. (1986), 34, 1, 115–118.

Biotech 84-05100, Mohr et al, Helv. Chim. Acta (1984), 67, 2, 406–412.

Biotech 82-02439, Lee et al, Phytopathology (1984) 72, 972.

*Primary Examiner*—Herbert J. Lilling
*Attorney, Agent, or Firm*—M. Howard Silverstein; John D. Fado; Mervin E. Brokke

[57] ABSTRACT

Mutants blocked or altered in the production of the trichothecene mycotoxin T-2 have been selected following UV mutagenesis of *Fusarium sporotrichioides* NRRL 3299. One mutant, NRRL 18339, accumulates the rare trichothecenes and dideacetylaclonectrin and deacetylcalonectrin. The second mutant, NRRL 18340, accumulates trichodiene, the first intermediate on the trichothecene biosynthetic pathway. These compounds are useful toxins or toxic precursors for the production of or investigation of immunotoxins for cancer therapy.

1 Claim, No Drawings

FUSARIUM SPOROTRICHIOIDES MUTANT STRAIN CAPABLE OF PRODUCING BOTH DIDEACETYLCALONECTRIN AND DEACETYLCALONECTRIN

BACKGROUND OF THE INVENTION

Targeting the delivery of toxins to malignant cells by complexing the toxin to monoclonal antibodies which recognize the cancer cells is becoming an effective approach to cancer therapy. The toxin-monoclonal antibody conjugates preferentially bind to and selectively kill the cancer cells [D.A. Vallera et al., Science 222: 512 (1983); E.S. Vietetta et al., Science 238; 1098 (1987)].

As a group, the trichothecenes appear to be promising toxins for the production of immunotoxins. The molecules are relatively small in size, and the class includes members with a wide range of toxic properties. Trichothecenes are potent inhibitors of protein synthesis [C.J. Carter and M. Cannon, Biochem. J. 166: 399–409 (1977); see also: Protection Against Trichothecene Mycotoxins, Natural Academy Press, Washington, DC pp. 129–138 (1983)]. This diversity provides the potential to design anticancer agents to meet specific requirements. There is a medically important need for a variety of trichothecenes.

Trichodiene was isolated from *Trichothecium roseum* [S. Nozoe and Y. Machida, Tetrahedron 28: 5105–5111 (1972)] and is the first intermediate in the trichothecene biosynthetic pathway. Dideacetylcalonectrin and deacetylcalonectrin are rare trichothecenes; these materials have heretofore been available only from complex synthetic methods or as minor components in fermentation broths [R. Greenhalgh et al., J. Agric. Food Chem. 34: 98–102 1986)]. It has not been previously economically feasible to produce these compounds in large quantity.

SUMMARY OF THE INVENTION

We have now discovered novel mutants selected following UV mutagenesis of *Fusarium sporotrichioides* NRRL 3299 which accumulate trichothecenes and trichodiene.

Mutant NRRL 18339 produces the trichothecenes dideacetylcalonectrin and deacetylcalonectrin; mutant NRRL 18340 accumulates trichodiene, the first intermediate on the trichothecene biosynthetic pathway.

In accordance with this discovery, it is an object of the invention to produce relatively high yields of dideacetylcalonectrin by a commercially feasible fermentation process.

A further object of the invention is to produce relatively high yields of deacetylcalonectrin by a commercially feasible fermentation process.

A further object of the invention is to produce relatively high yields of trichodiene by a commercially feasible fermentation process.

A further object of the invention is to define two novel mutant species of Fusarium which are capable of producing trichothecenes and trichodiene.

Other objects and advantages of this invention will become readily apparent from the ensuring description.

DETAILED DESCRIPTION OF THE INVENTION

The fungal strains used in this invention were derived by UV mutagenesis of *Fusarium sporotrichioides* NRRL 3299 (ATCC 24043) deposited with the ARS Culture Collection, Peoria, IL. This strain was originally isolated from corn in France.

Microconidia are obtained for mutagenesis as follows. Frozen glycerol stocks of conidia are inoculated, after thawing, on agar plats, which are then incubated for several days. This results in cultures which produce primarily one- and two-celled microconidia. The microconidia thus obtained are then exposed to UV light and incubated in the dark for several days. Surviving colonies are then screened for T-2 production using the monoclonal antibody technique developed by Hunter et al. and modified by Beremand [K.W. Hunter et al., Appl. Eviron, Microbiol. 49: 168-172 (1985), and M. N. Beremand, Appl. Environ. Microbiol. 53: 1855-1859 (1987)]. Mutants which are blocked or altered in the biosynthesis of T-2 toxin are selected and further examined for the production of other trichothecene compounds.

Using the above technique, two novel mutant species were discovered which produce relatively large quantities of rare trichothecenes and related materials. Mutant strain NRRL 18339 produces 15-deacetylcalonectrin (Compound 1) and 3,15-dideacetylcalonectrin (Compound 2). Strain NRRL 18340 accumulates trichodiene (Compound 3) and does not produce any 12,13-epoxy-trichothecenes. These two mutant species are deposited with the ARS Culture Collection, Peoria, IL.

To prepare quantities of the heretofore rare trichothecene derivatives, conidial suspensions are prepared from 1- to 2-week-old cultures grown on solid media.

A growth medium comprising glucose, 5-10%, preferably 5%; yeast, 0.1–0.2%, preferably 0.1%; peptone, 0.1–0.2%, preferably 0.1%, is prepared and inoculated with conidia to a level of $10^3$–$10^5$, preferably $5 \times 10^4$ per ml. The cultures are incubated from 5 to 14 days, preferably 14 days, at 25–30° C., preferably 28° C.

Analyses indicate 100 to 1000 μM/L of products are produced under the above conditions.

The trichothecenes and trichodiene may be isolated by standard techniques such as solvent extraction of the culture, including both cellular material and growth media, and subsequent purification by chromatographic procedures.

Analysis of samples by gas chromatography-mass spectrometry (GC/MS) verified that the compound produced by mutant NRRL 18340 was trichodiene.

Small quantities of compounds 1 and 2 were isolated by preparative thin layer chromatography from a 7-day-old 25 ml liquid shake culture of mutant NRRL 18339. Analysis of these compounds by GC/MS demonstrated that both compounds contained the 12,13-epoxy-trichothec-9-ene nucleus and thus confirmed that they were trichothecenes. The chemical ionization mass spectra of trimethylsilyl-derivatized and underivatized samples further revealed that compound 1 contained a free hydroxyl group and an acetate, while compound 2 contained 2 hydroxyl groups.

The structures of compounds 1 and 2 were determined by NMR analysis of larger amounts of these compounds which were purified from the culture filtrate of a 4 L liquid fermentation of strain NRRL 18339. Based on the $^1$H and $^{13}$C-NMR spectra, compounds 1 and 2 were identified as 15-deacetylcalonectrin (DECAL) and 3,19-dideacetylcalonectrin (DIDECAL).

Both compounds contain 2 less oxygen moieties than found in T-2 toxin.

Finally, GC and GC/MS analyses of crude ethyl acetate extracts of NRRL 18339 revealed that this mutant produces small amounts of T-2 toxin. Thus NRRL 18339 appears to be a slightly leaky mutant.

Liquid cultures were left intact or separated by filtration into mycelia and filtrate fractions prior to extraction with ethyl acetate. GC analysis of these samples demonstrated that all of the T-2 toxin produced by the wild type parent was excreted into the medium (Table 1). In contrast, 100% of the trichodiene produced by NRRL 18340 remained associated with the mycelia. The calonectrin analogues produced by NRRL 18339 displayed an intermediate response; 60 to 70% of these two compounds was isolated from the culture filtrate, and the remaining 30 to 40% was isolated from the mycelial fraction.

Measurement of radial colony growth rate on V8-juice agar and M-100 minimal medium revealed that the mutant strains were prototrophic and that they retained wild type growth rates. Likewise, growth of the mutants in liquid shake cultures, as measured by mycelial dry weights, was indistinguishable from that of the wild type parent. Gross morphology of the mutant and the wild type cultures were the same for all strains growing on solid and liquid media.

Without desiring to be bound by any theory of operation, it is believed that the inability of the mutant to produce T-2 toxin is associated with changes in conidiation. Both mutants produce two- to sixfold fewer conidia than the wild type parent when grown on V-8 juice agar medium. In addition, the nontrichothecene, trichodiene accumulating mutant also produces conidia with an altered morphology. A diagnostic species trait of F. sporotrichioides is the formation of napiform or pear-shaped microconidia. Mutant NRRL 18340 fails to make napiform conidia when grown on V8-juice agar. The inability to make napiform conidia can be reversed when NRRL 18340 is grown in the presence of exogeneously supplied T-2 toxin. Furthermore, T-2 toxin appears to be required during conidiation.

TABLE I

Localization of Trichodiene and Trichothecenes Accumulated by Wild Type and Mutant Strains of *Fusarium sporotrichioides* Grown in Liquid Shake Cultures[a]

| Sample | NRRL 18340 Trichodiene ($\mu$g/ml) | NRRL 18339 Didecal ($\mu$g/ml) | NRRL 18339 15-Decal ($\mu$g/ml) | NRRL 3299 T-2 Toxin ($\mu$g/ml) |
|---|---|---|---|---|
| Whole culture | 126 | 127 | 80 | 265 |
| Mycelia | 122 | 39 | 30 | 0 |
| Filtrate | 0 | 88 | 50 | 292 |

[a]YEPD-5G media was inoculated to a final density of 5–7 × 10⁴ conidia per ml and incubated 7 to 8 days at 28° C. and 180–200 rpm.

NRRL 18340 conidia formed in the absence of T-2 toxin are not converted to pear-shaped conidia by subsequent incubation (for up to 24 hrs) with T-2 toxin. Addition of T-2 toxin to the wild type and mutant NRRL 18339 also appears to stimulate production of napiform conidia in these strains. Addition of T-2 toxin does not, however, restore the level of conidia production in either NRRL 18340 or NRRL 18339 to that observed for the wild type parent. The above results provide the first indication that trichothecenes may play a role in fungal development.

The following examples are intended only to further illustrate the invention and are not intended to limit the scope of the invention which is defined by the claims.

EXAMPLE 1

UV Mutagenesis and Mutant Screen

Microconidia were obtained from V-8 agar plates that were incubated for 4 days following inoculation with approximately $2.5 \times 10^6$ freshly thawed conidia from frozen (−70° C.) glycerol stocks. This procedure yielded primarily one- and two-celled microconidia, with approximately 65% of the total being one-celled. The microconidia were exposed to UV light (254 nm) on agar plates until 90% kill was achieved [see J. Avalos et al., Appl. Environ. Microbiol. 49: 187-191 (1985) and Beremand, supra].

The UV-treated plates were immediately placed in the dark and incubated for 2 to 3 days in the growth chamber. To screen for T-2 toxin production, a portion of each surviving colony was transferred to a well in a 96-well microtiter plate (Falcon 3072; Becton Dickinson Labware, Oxnard, Calif.) containing 150 $\mu$l of YEPD-5G per well. The plates were sealed with Parafilm to reduce evaporation and were incubated at 28° C. at 50 to 60 rpm on a minishaker (Dynatech Laboratories, Inc., Alexandria, VA). After 4 to 5 days, the fungal mat was removed from each well with a toothpick to yield a cleared supernatant. The supernatants were stored at −20° C. until the immunoassays were performed. For the immunoassays, each microtiter plate contained a blank control well (which yielded an $A_{410}$ value for media only), a positive well (which yielded an $A_{410}$ value for a T-2 toxin standard solution containing $2 \times 10^{-4}$ M T-2), and 94 test samples (culture filtrates). Colonies which produced test samples that yielded an $A_{410}$ value either equal to that of the blank control or significantly higher than that of the T-2 control were scored as potential toxin mutants. To screen for auxotrophy, strains were tested for their ability to grow on M-100 minimal medium.

Competitive inhibition enzyme-linked immunoassays (CIEIAs) were performed with affinity-purified monoclonal antibody 15H6 as described by Hunter et al., supra, except that methanol could be omitted from the phosphate-buffered saline-Tween 20 solution without consequence. A fraction of the culture supernatant, the T-2 standard solution, or the control medium (50 $\mu$l) was mixed in polystyrene microtiter plates (Falcon 3190) with 50 $\mu$l of 15H6 monoclonal antibody diluted to 5 $\mu\mu$g/ml in phosphate-buffered saline containing 0.05% Tween 20. Following incubation for 1 hr at room temperature, fractions (50 $\mu$l) of these samples were transferred to the wells of round-bottom polyvinyl microtiter plates (Dynatech) with T-2-bovine serum albumin (10 $\mu$g/ml in 0.1 M Tris hydrochloride [pH 8.2]; Sigma Chemical Co., St. Louis, MO) by overnight incubation at 4° C. After 30 min of incubation at room temperature, the wells were washed five times with phosphate-buffered saline-0.05% Tween 20 and successively incubated with rabbit anti-mouse kappa light chain antiserum (ICN Immuno chemicals, Elkhart, IN), goat anti-rabbit immunoglobulin G-alkaline phosphate conjugate (Sigma), and enzyme substrate (p-nitrophenylphosphate; Sigma) as described previously (9). Assays were measured at 410 nm on an automatic microtiter plate reader (Dynatech).

EXAMPLE 2

Culture Growth Conditions

Cultures were grown on V-8 agar medium slants or plates on an alternating 12-hr 25° C. light/20° C. dark schedule. For long-term storage, strains were maintained on V-8 agar slants at 4° C. and were stored as conidial suspensions in 10 to 15% (vol/vol) glycerol at −90° C. For all assays, fresh transfers of the strains were obtained from stock cultures stored at 4° C.

Trichothecene production was measured in liquid shake cultures. Conidial suspensions were prepared from 1- to 2-week-old cultures grown on V-8 juice agar plates. 2.8-Liter Fernback flasks containing 1 L of 5% glucose-0.1% yeast extract-0.1% peptone were inoculated with conidia to a final concentration of $10^4$ per ml. Cultures were incubated at 200 rpm on a gyratory shaker. Incubation was continued as described above for a total of 7 days, at which time the products were isolated and analyzed.

EXAMPLE 3

Instrumentation for Analysis

Trichothecenes and trichodiene were identified and quantitated by gas chromatography (GC)-mass spectrometry (MS) with a mass spectrometer (TSQ46; Finnegan). Electron ionization (EI) spectra were obtained at 70 V. Chemical ionization (CI) spectra were recorded at a measured source temperature of 100° C. Isobutane (0.3 torr) was the reagent gas. Conventional mass spectra were obtained by operating the first two quadrupoles in the all-pass mode and scanning the third quadrupole. In tandem MS experiments, the protonated molecule (MH+) was selected by quadrupole 1, and daughter fragments were formed in quadrupole 2 by collision with argon (1 mtorr and 20 V). The resulting daughter ions were mass analyzed by the third quadrupole.

GC/MS analyses were made on either a capillary or a packed column. A fused silica capillary column (30 M by 0.25 mm; DB-1; J&W Scientific, Rancho Cordova, CA) was used. The linear flow rate of helium in the column was 50 cm/s. The injection port temperature was held at 250° C. Samples were injected in the split mode with a split ratio of approximately 90:1. The outlet of the capillary column was directly coupled into the source of the mass spectrometer. The packed column was a glass column (2m×2 mm) packed with 1% OV-1 on 100-200 mesh Chromosorb W. The flow rate was 20 ml/min, and the column was coupled to the mass spectrometer via a glass jet separator.

EXAMPLE 4

Trichothecene Analysis

Trimethylsilyl derivatives were made from 50-μl portions of the culture media extracts by evaporation of the ethyl acetate under nitrogen and the addition of 50 μl of Tri-Sil/TBT (Pierce Chemical Co., Rockford, IL). The samples were held at 50° C. for 1 hr before 1 μl was analyzed by GC/MS. For capillary GC/MS, the starting GC temperature was 180° C. At 2 min after injection, the column was heated at 6° C./min to a final temperature of 270° C.; it was then held at this temperature. When used in the CI mode, the mass spectrometer was scanned from 90 to 700 daltons. In the EI mode, the mass spectrometer was scanned from 40 to 700 daltons. Repetitive scans of 1 s were acquired, and GC peaks were detected form the reconstructed ion chromatogram and were identified by comparison with standards. For a more rapid quantitative method, the packed column was programmed from 200°-250° C. at 10° C./min. The protonated molecular ion and the most intense ion for the compounds of interest were monitored in the selected ion mode. Response factors were determined from linear regression of the response from injection of known amounts of these compounds across the range of 1 ng to 10 μg and were used to quantitate the amount of individual trichothecenes in the samples. The total analysis time with the packed column was less than 6 min per sample.

EXAMPLE 5

Trichodiene Analysis

The culture extracts were analyzed for trichodiene without derivatization. The samples were injected into packed or capillary columns at 120° C. and after 5 min the column over temperature was raised to 250° C. at 4° C./min. Trichodiene was identified in the culture extracts based on comparison the EI and CI mass spectra and the daughter ion spectrum of the protanated molecule with those for the chemically synthesized and the biosynthetically produced standards [Van Middlesworth et al., J. Chem. Soc. Chem. Commun. 1986: 1156-1157]. The EI spectrum (FIG. 1) had a weak molecular ion (m/z 204). The most abundant fragment at m/a 109 was created by cleavage between the two rings. The intense dimethyl cyclohexadiene fragment at m/z 108 arose from the transfer of a hydrogen to the vinyl group and cleavage between the two rings. The isobutane CI spectrum (FIG. 1) of trichodiene has an intense protonated molecule (m/z 205) and two intense fragments at m/z 95 and m/z 109 which resulted from cleavage between the two rings. The daughter spectrum of the protonated molecule had only two abundant fragments, the m/z 109 and m/z 95 ions. The retention times and mass spectra for the trichodiene standard and for trichodiene in the ancymidol-treated cultures were identical. Close examination of CI spectra from chromatograms of extracts from ancymidol-treated cultures revealed a complex pattern of minor sesquiterpenoid components with signals at m/z 205. However, none of these minor components had intense m/z 109 signals or any detectable daughters of the m/z 205 parent at m/z 109 in MS/MS scans. Quantitation of the amount of trichodiene in ancymidol-treated culture extracts was based on the use of external standards. For quantitative analyses, three ions, m/z 205 ($MH^+$), m/z 109, and m/z 95, were measured by selected ion monitoring in the CI mode. The size of the m/z 109 fragment was used to determine the amount of trichodiene in the culture extracts. The response of the m/z 109 signal at the proper retention time for trichodiene was linear across the range from 1 ng to 2 μg. Typical coefficients of variation for replicate analyses were between 8 and 15%.

EXAMPLE 6

Isolation of Trichothecenes

A 4-L culture of the mutant NRRL 18339 was extracted twice with an equal volume of ethyl acetate. The combined extracts were evaporated to dryness and resuspended in 20 ml of ethyl acetate. This extract was separated on a preparative silica cartridge using a Waters prepmaster liquid chromatograph. The column was eluted with $CH_2Cl_2$/methanol (98/2).Eighteen 500-ml fractions were collected. Then the column was washed with 500 ml of methanol. The separation was monitored by TLC. Fractions 7 and 8, which contained Compound 1 (below), were combined for additional purification. Compound 2 (below) was found by TLC to be in the methanol (fraction 19). This fraction was reapplied to the silica cartridge and eluted with $CH_2Cl_2$/methanol (95/5). Fourteen 500-ml fractions were collected and then the column was washed with 500 ml of methanol. Compound 2 was shown to be in fractions 4 and 5, which were combined for further purification.

Compound 1: Deacetylated calonectrin

Compound 2: Dideacetylated calonectrin

The combined fractions containing Compound 1 were purified further by JPLC on a Whatman PAC column. The separation was developed on an analytical column (20 cm×4.6 mm) and then preparative separations were made using the "Magnum-9" column (50 cm ×9.5 mm). The eluting components were detected with a differential refractometer. Compound 1, 37 mg, was isolated from repeated injections of portions of the fraction containing it. The solvent was hexane/ethyl acetate (60/40). It eluted as a peak with a retention of about 3 column volumes. Compound 2, 26 mg, was isolated from fractions containing it. Hexane/ethyl acetate (25/75) was the solvent.

EXAMPLE 7

Large Scale Production of Trichodiene

Each of three flasks containing autoclaved rice (333 g) was inoculated with an 11-ml aliquot of a 48-hr-old liquid shaker culture which had been inoculated with $5 \times 10^4$ conidia and incubated for 2 weeks at 28° and 200 rpm. The entire culture was extracted three times with three volumes of ethyl acetate.

The combined ethyl acetate extracts were evaporated to yield an oily residue which was applied to a 3-in pad of silica gel in a scintered glass funnel (7.0 cm×9.5 cm id). The trichodiene was eluted from the gel with hexane and was present in the first 700 ml collected. A total of 10 g of trichodiene was thus obtained.

Compound 3: Trichodiene

It is understood that the foregoing detailed description is given merely by way of illustration and that modification and variations may be made therein without departing from the spirit and scope of the invention.

We claim:

1. A *Fusarium sporotrichioides* mutant strain having the identifying characteristics of ARS Culture Collection Accession No. 18339; said strain being capable of producing dideacetylcalonectrin and deacetylcalonectrin in amounts greater than 100 μm/L.

* * * * *